(12) United States Patent
Koest

(10) Patent No.: US 6,220,708 B1
(45) Date of Patent: Apr. 24, 2001

(54) METHOD AND DEVICE FOR PRODUCING MULTICOLORED PATTERNS

(75) Inventor: Gert Koest, Hannover (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

(21) Appl. No.: 09/510,743

(22) Filed: Feb. 22, 2000

(30) Foreign Application Priority Data

Mar. 11, 1999 (DE) ............................................. 199 10 743

(51) Int. Cl.[7] .......................................................... A61B 3/02
(52) U.S. Cl. ............................................. 351/242; 351/243
(58) Field of Search ..................................... 351/221, 222, 351/232, 233, 234, 235, 237, 238, 239, 242, 243, 246; 348/742, 743

(56) References Cited

U.S. PATENT DOCUMENTS 4,090,219 * 5/1978 Ernstoff et al. ....................... 348/742
5,550,602 * 8/1996 Braeuning ............................ 351/243

* cited by examiner

*Primary Examiner*—George Manuel
(74) *Attorney, Agent, or Firm*—Flynn, Thiel, Boutell & Tanis, P.C.

(57) ABSTRACT

A method and device for producing multicolored patterns can test the color vision or the reaction of a viewer. The patterns are produced by at least one switchable light source and at least two differently colored transparent color segments, which are alternately moved into the beam path of the light source. The device is a technically simple and inexpensive method to create multicolored patterns. In this manner, the light source or the light sources shine through each color segment of the color screen at a time interval predetermined by a control so that individual colors are produced. The time intervals of the individual colors follow one another so quickly that a color-merging frequency is reached or exceeded, and the individual colors of each individual light source merge into a mixed color.

22 Claims, 3 Drawing Sheets

METHOD AND DEVICE FOR PRODUCING MULTICOLORED PATTERNS

FIELD OF THE INVENTION

The invention relates to a method and a device for producing multicolored patterns, for example, patterns for testing the color vision or the reaction by means of at least one switchable light source and at least two differently colored, transparent color segments, which are moved alternately into the beam path of the light source.

BACKGROUND OF THE INVENTION

In order to test the color vision of a person, ophthalmologist and optometrists often use Ishihara images, which images are named after their developer. These are patterns of colored dots, which are presented to the person being tested. If the person recognizes the patterns, the person being tested may lack color recognition in this area. The lack of color recognition is possible in various degrees and expressions. The most familiar expression is the red-green weakness in men. In order to be able to determine the exact extent of the color blindness, a plurality of Ishihara images are needed. At a time of testing, the course of testing, which has so far taken place, is thereby important and determines which images will be presented to the person being testing during the further course of testing. In order to be able to cover the entire spectrum of the possible color blindness, an ophthalmologist or an optometrist must therefore have available a plurality of Ishihara images. The images, which as a rule are collected in books, are however, expensive to purchase. It is furthermore complicated to manually select the images necessary for the respective next step of testing from the plurality of existing images.

An alternative to the printed Ishihara images would be, for example, dias of the Ishihara images, which would be projected onto a screen by a slide projector. However, even when using slide transparencies, the problem of the scope, the image collection or the unsatisfactory possibility of the control of the sequence of the color vision test would continue to exist.

Also, as an alternative, it would be conceivable to use a picture screen, such as a LCD picture screen or a classic tube screen. However, these would be too expensive in relationship to their purpose so that the use of a picture screen to data does not represent a satisfactory alternative to the printed Ishihara images.

A device of the above-mentioned type, however, is not limited to the production of Ishihara images. Rather any desired patterns can be created with such a device. These may also, in the case of one single light source, be timed patterns of signals from the light source.

The purpose of the invention is therefore to provide a technically simple and inexpensive method and a vision-testing device, with which multicolored patterns can be produced. Whereby, in particular, a quick flexible automatic change between the multicolored patterns is possible.

SUMMARY OF THE INVENTION

This purpose is attained according to the invention in such a manner that the light source or the light sources shine through each color segment in a time interval predetermined by a control and individual colors are produced in this manner, whereby the time intervals of the individual colors follow one another so quickly that the color-merging frequency is reached or exceeded. The individual colors of each individual light source merge into a mixed color so that a flicker-free image is created.

A light beam, which starts out from a light source, thus moves through a color segment. Such a color segment may, for example, be a transparent foil. From there, the now colored light beam enters the eye of a viewer. Various color segments are now alternately moved into the light beam. This is done so quickly that the eye can no longer recognize the change between the individual color segments. A mixed color is thus created in the eye of the viewer from the colors of the color segments which are moved into the light beam. The time intervals, during which the light source thus shines through the color segments, must be shorter than the color-merging frequency of the eye. The method is made possible by the inertia of the eye.

An advantageous further development of the invention is that the color segments can be moved in equal time intervals into the beam path of each light source, and the switch-on duration of the light sources is controlled individually for each individual light source and for each individual color segment. It is advantageous when the color segments are parts of a circular color screen which is rotated about its center axis, and the light sources which shine through the color screen or the color segments of the color screen, are light diodes. The light diodes are then arranged parallel in a plane with respect to the color screen, and the control regulates the speed of the color screen and controls the switch-on duration of each individual light diode for each individual color segment.

A further advantageous development of the method is that the light source is continuously switched on and the color segments are moved into the beam paths of the light sources for varying times.

A device of the invention, which attains the set purpose, has at least one switchable light source and at least two transparent color segments which can be moved alternately into the beam path of the light source. The set purpose is attained in such a manner that the color segments form parts of a circular color screen which can be rotatably driven about the center axis and above the light source. A control is provided with which the rotational speed of the color screen can be regulated. The switch-on duration of each individual light source can be controlled for each color segment.

The light sources can, according to the invention, be light emitting diodes. Particular advantageous are white light diodes.

The light sources can, according to the invention, be arranged in one plane parallel to the color screen. It is thereby advantageous that the light sources are arranged in one line radially with respect to the axis of rotation of the color screen or are arranged matrix-shaped.

A special embodiment of the invention makes it possible to control the light intensity of each individual light source with the control. The device also can, according to the invention, be protected against stray or scattered light leakage by a housing having a viewing window. It is possible thereby to arrange only the light sources and the color screen in the housing. The device can, according to the invention, be a part of an anomaloscope of a projector, a vision-testing device or a reaction-testing device.

The purpose of the invention can be attained in a vision-testing device, in particular a vision-testing device with a clear view, which is provided with an imaging device of a test object provided within the focal distance of the imaging device and being reproducible at varying distances or intervals. In order to produce the test object, a device is provided having at least one switchable light source and at least two transparent color segments. The color segments must be movable alternately into a beam path of the light source, and the color segments must form parts of a circular color screen. The color screen can be driven rotatably about its center axis. A control can regulate the speed of the color screen and control the switch-on duration of each individual light source for each color segment.

Such a vision-testing device can advantageously have an optic deflecting device in the beam path between the imaging or reproducing device and the test object, which deflects the beam path at 180° into two beam-path fragments. This optic deflecting device can then be moved in the direction of the two thus formed beam-path fragments, which are parallel to one another, and the test object is constructed nonmovably in this direction. The optic structural elements lying in the beam path have a width such that, even in the case of a large spacing between the pupils of a person being tested, both eyes can participate in the test. In order to produce further test objects, it is possible to provide a test screen or drum, with a plurality of testing fields, which can each be moved as an instantaneous test object into the beam path.

BRIEF DESCRIPTION OF THE DRAWINGS

One exemplary embodiment will be described in greater detail in connection with the drawings, in which.

DETAILED DESCRIPTION OF THE INVENTION

Figure 1:
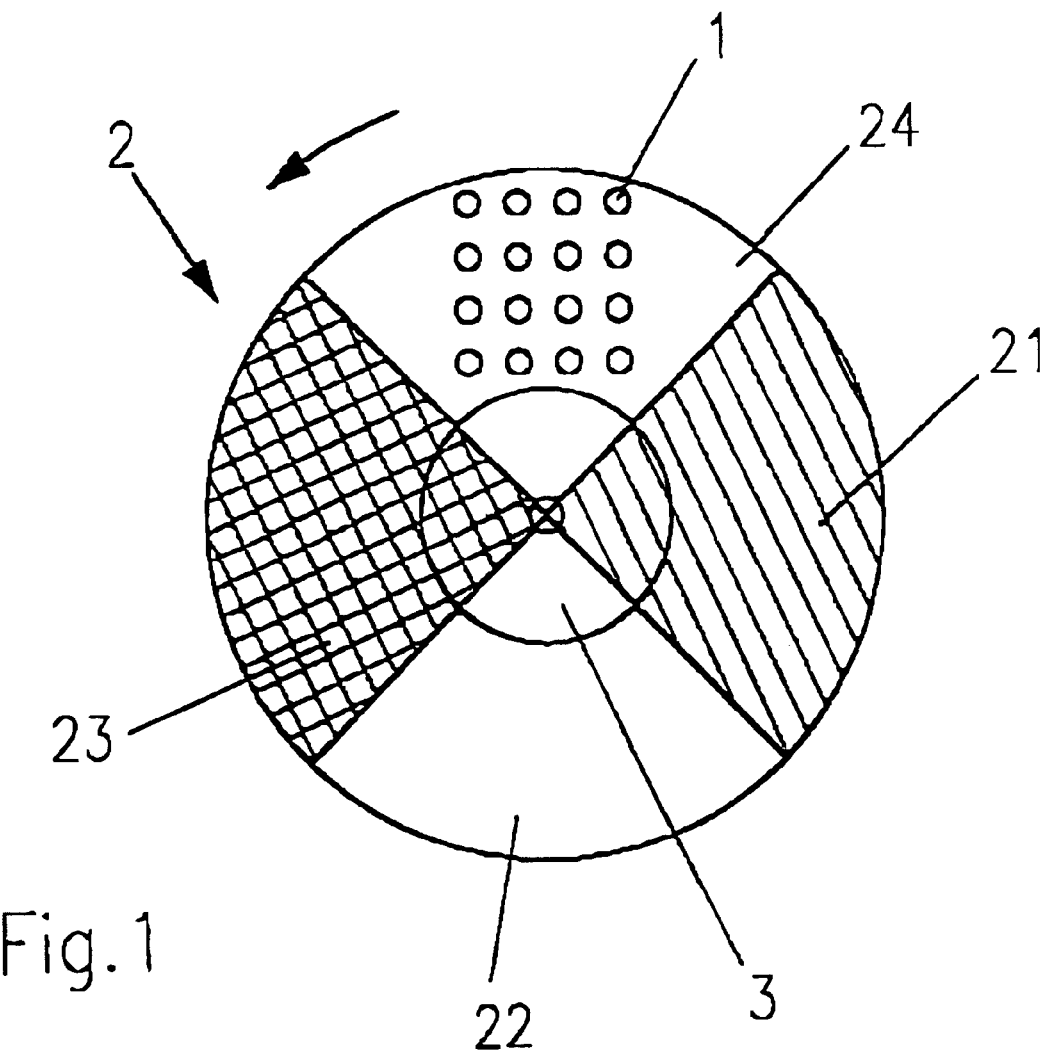
FIG. 1 is a schematic top view of a device of the invention.
Figure 2:
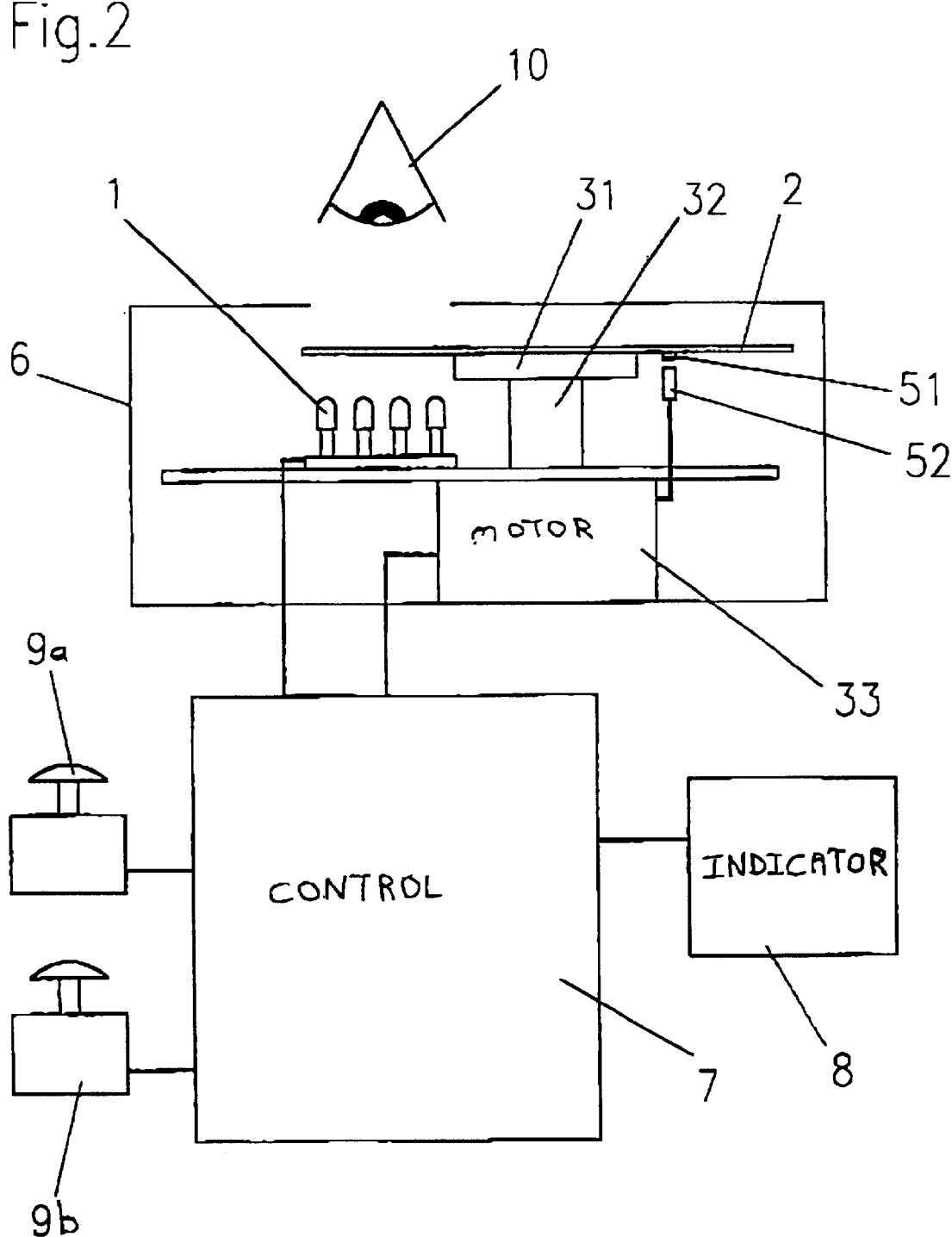
FIG. 2 is a schematic illustration of the entire device.

The color screen 2 illustrated in FIG. 1 has four color segments 21, 22, 23, 24, which each have a portion of 90° of the color screen. The color segments are fastened on the hub 31. The hub 31 is connected to the motor 33 via the axle 32. The color or test screen 2 is driven by the motor 33. Light sources or diodes 1 are arranged in matrix form in a plane parallel to and below the color screen 2.

Housing 6 having a viewing window receives and contains the light sources 1 and the color screen 2. The light diodes 1 and the motor 33 are connected to a control or controller. The control 7 preferably comprises a computer, microprocessor or other digital circuits. The control stores a large number of Ishihara images. The sequence of images displayed by the device is decided or selected by the control 7. The control 7 controls, on the other hand, the switch-on times of the light diodes 1 and on the other hand, regulates the motor 33. To detect the speed of the motor 33, an impulse transmitter 51 is fastened to the color screen 2. The impulse transmitter rotates with the color screen and passes thereby per rotation once over the sensor 52. The sensor registers the rotation and emits a signal to the control 7. Thus, the control 7 can detect the speed of the color screen 2 and can correct the speed of the motor 33 accordingly. The sensor 52 can, in cooperation with the impulse transmitter 51, however, also be used to adjust an initial position of the color screen 2.

Furthermore, two keys, such as actuators 9a, 9b, are connected to the control 7, which keys are used to operate the device. Furthermore, an indicator 8 is connected to the control 7, so that significant values regarding the state of the device or the course of the test can be indicated.

Figure 3:
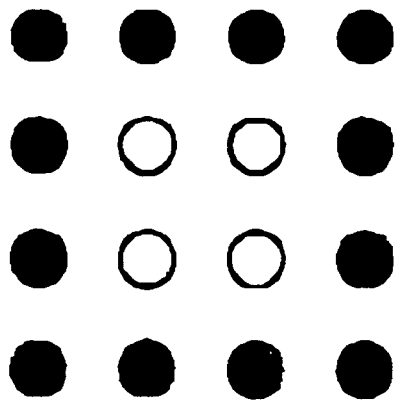
FIG. 3 shows a first example for a producible pattern.
Figure 4:
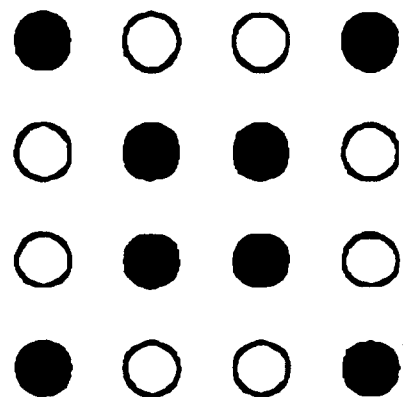
FIG. 4 shows a second example for a producible pattern.

The illustrated exemplary embodiment is operated at a constant motor speed. Depending on which of the four color segments 21 to 24 is positioned above the light diode 1 and depending on which color is supposed to be produced, this diode 1 is switched on and again turned off. The change between the colors occurs so quickly that a color-merging frequency is thereby reached or exceeded. These light diodes appear than as colored light diodes in the eye of a viewer 10. Since each light diode is individually controlled, it is possible to produce with the diodes varying colors and thus any desired colored patterns. Two such patterns, for example, are illustrated in FIGS. 3 and 4.

The sequence of a color-vision test can, for example occur as follows: A specific Ishihara image is produced with the device. The test person recognizes this Ishihara image and acknowledges same with one of the keys 9a. The control 7 thereafter calls up the next predetermined Ishihara image. However, if the test person 10 does not recognize same, he/she operates the other key 9b, thus acknowledging the image negatively. The control 7 recognizes consequently that a weakness exists here in the test person 10. In order to more exactly define this weakness, the control 7, in response to the previously displayed Ishihara image and the test key 9a, 9b actuated, selects and displays a suitable Ishihara image. This Ishihara image is produced with the light diodes 1 and the test screen 2. Again the test person 10 has to decide whether he/she recognizes or does not recognize the Ishihara image. Depending on this, he/she will operate one of the keys 9a, 9b, and thus determine the further course of the images to be selected by control 7 until the color-vision test ends. At the end, it is possible for an optometrist or ophthalmologist to read the result of the test on the indicator 8. The test result can also be stored in control 7. A complicated handling of the test with books is no longer needed.

Although particular preferred embodiments of the invention has been disclosed in detail for illustrative purposes, it will be recognized that variations or modifications of the disclosed apparatus, including the rearrangement of parts, lies within the scope of the present invention.

What is claimed is:

1. A method for producing multicolored patterns for testing the color vision or the reaction of a viewer by means of at least one switchable light source and at least two differently colored, transparent color segments, which are moved alternately into beams coming from that at least one light source, wherein the at least one light source shines through each color segment during a time interval predetermined by a control to produce individual colors, whereby the time intervals of the individual colors follow one another so quickly that a color-merging frequency is reached or exceeded, and the individual colors of the at least one light source merge into a mixed color and create a flicker-free image.

2. The method according to claim 1, wherein the at least one light source comprises one of a plurality of individual light sources and the color segments are moved in equal time intervals into the beam paths of the light sources, and the switch-on duration of the light sources is controlled individually for each of the individual light sources and for each individual color segment.

3. The method according to claim 2, wherein the color segments form parts of a circular color screen and the color screen is driven about its center axis, the plurality of light sources comprise light diodes which shine through the color segments and are arranged in a plane parallel with respect to the color screen, and the control regulates the speed of the color screen and controls the switch-on duration of each light diode for each individual color segment.

4. The method according to claim 1, wherein the at least one light source is continuously switched on, and the color segments are moved into the beam path of the at least one light source for varying times.

5. A device for producing multicolored patterns for testing the color vision or the reaction of a viewer including at least one switchable light source and at least two transparent color segments which are capable of being moved alternately into a beam path of the at least one light source, wherein the color segments form part of a circular color screen which is drivable rotatably about an axis lying perpendicular thereto and a control controls the speed of the color screen and regulates the switch-on duration of the at least one light source for each color segment.

6. The device according to claim 5, wherein the at least one light source is a light diode.

7. The device according to claim 6, wherein the at least one light diode is white.

8. The device according to claim 6, wherein the light intensity of the at least one light source is adjustable by the control.

9. The device according to claim 5, wherein the at least one light source comprises one of a plurality of light sources, and wherein the light sources are arranged in a plane parallel with respect to the color screen.

10. The device according to claim 9, wherein the light sources are arranged in a line radially with respect to the axis of rotation of the color screen.

11. The device according to claim 10, wherein the light sources and the color screen are arranged in a housing with a viewing window.

12. The device according to claim 9, wherein the light sources are arranged in a matrix-shape.

13. The device according to claim 9, wherein the light sources and the color screen are arranged in a housing with a viewing window.

14. The device according to claim 5, wherein the light intensity of the at least one light source is adjustable by the control.

15. The device according to claim 5, wherein the device is part of an anomaloscope, a projector, a vision-testing device, or a reaction-testing device.

16. A vision-testing device including an imaging device for reproducing a test object provided within the focal distance of the imaging device and reproducible at varying distances, wherein to produce the test object, a device is provided including at least one switchable light source and at least two transparent color segments, wherein the color segments are alternately movable into a beam path of the at lest one light source, and the color segments comprise parts of a circular color screen capable of being rotatably driven about its central axis, and a control regulates the speed of the color screen and controls the switch-on duration of the at least one light source for each color segment.

17. The vision-testing device according to claim 16, wherein an optic deflecting device is provided in a beam path between the imaging device and the test object for deflecting the beam path at 180°, and is movable in a direction of two so formed beam path fragments, which are parallel to one another, and the test object is constructed nonmovably in the direction, and optic structural elements lying in the beam path enable large spacing between the beam path fragments so that both eyes of the viewer are capable of participation in a vision test.

18. The vision-testing device according to claim 17, wherein, in order to produce further test objects, a testing screen or drum is provided which includes a plurality of testing fields for movement of an instantaneous test object into the beam path.

19. The vision-testing device according to claim 16, wherein in order to produce further test objects, a testing screen or drum is provided which includes a plurality of testing fields for movement of an instantaneous test object into a beam path.

20. An apparatus for producing a sequence of multicolored patterns for testing the color vision or the reaction of a viewer comprising:

at least one light source;

at least two differently colored, transparent segments for movement into beams coming from the at least one light source;

first and second actuators for selective actuation by the viewer in response to viewing of a multicolored pattern generated by said at least one light source and said at least two segments; and a control for storing a plurality of multicolored patterns and controlling said light source and said transparent segments to display a selected one of the stored patterns, said control, in response to the selective actuation of one of the first and second actuators, controlling said at least one light source and said at least two transparent segments to display a different one of the stored plurality of multicolored patterns.

21. The apparatus of claim 20, including an indicator for displaying a result of the testing for color vision.

22. The apparatus of claim 20, wherein the multicolored patterns are Ishihara images.

* * * * *